(12) United States Patent
Kulikov

(10) Patent No.: US 6,613,027 B2
(45) Date of Patent: Sep. 2, 2003

(54) URINE COLLECTING METHOD AND ASSEMBLY FOR INCONTINENT MALES

(76) Inventor: Vyacheslav Kulikov, 30 Pleasant St., Apt. 121, Lynn, MA (US) 01902

( * ) Notice: Subject to any disclaimer, the term of this patent is extended or adjusted under 35 U.S.C. 154(b) by 115 days.

(21) Appl. No.: 09/882,711

(22) Filed: Jun. 18, 2001

(65) Prior Publication Data

US 2002/0193763 A1 Dec. 19, 2002

(51) Int. Cl.[7] .............................. A61F 5/44; A61M 5/32
(52) U.S. Cl. ...................... 604/353; 604/349; 604/350; 604/345; 604/174
(58) Field of Search .................................. 604/350, 353, 604/349, 345, 174

(56) References Cited

U.S. PATENT DOCUMENTS

| | | | | |
|---|---|---|---|---|
| 4,106,490 A | * | 8/1978 | Spilman et al. | 600/574 |
| 4,557,274 A | * | 12/1985 | Cawood | 600/573 |
| 4,713,067 A | * | 12/1987 | Rothenberg et al. | 24/30.5 R |
| 4,846,816 A | * | 7/1989 | Manfredi | 604/323 |
| 5,478,334 A | * | 12/1995 | Bernstein | 604/345 |
| 5,593,389 A | * | 1/1997 | Chang | 128/DIG. 26 |
| 5,797,890 A | * | 8/1998 | Goulter et al. | 604/351 |
| 5,897,540 A | * | 4/1999 | Grundke et al. | 604/349 |
| 6,010,489 A | * | 1/2000 | Blackburn | 604/349 |
| 6,066,112 A | * | 5/2000 | Quinn | 604/174 |
| 6,113,582 A | * | 9/2000 | Dwork | 604/349 |
| 6,248,096 B1 | * | 6/2001 | Dwork et al. | 604/347 |

* cited by examiner

Primary Examiner—William C. Doerrler
Assistant Examiner—Filip Zec
(74) Attorney, Agent, or Firm—Boris Leschinsky

(57) ABSTRACT

The urine collecting assembly is provided having a urine receptacle and a urine collector. In the provided assembly, the urine receptacle has a male organ enclosing case with an outer vertical flange, an inner vertical flange and an outer horizontal flange. The urine receptacle also has a catheter connected to the case of the receptacle with its inner horizontal flange, this inner horizontal flange being mounted on the outer horizontal flange means of the case. The urine collector of the present invention has a collecting compartment and is connected to the catheter of the receptacle with a connecting tube. The outer vertical flange of the case of the receptacle is supporting the male organ of the patient so that the inner vertical flange of the case and the inner horizontal flange of the catheter are preventing the flow-back of the urine, thereby keeping the pubic area of the patient free of moisture. The provided assembly is secured on the patient's body by a waistband and a belt set, displaced between the waistband and the assembly.

8 Claims, 3 Drawing Sheets

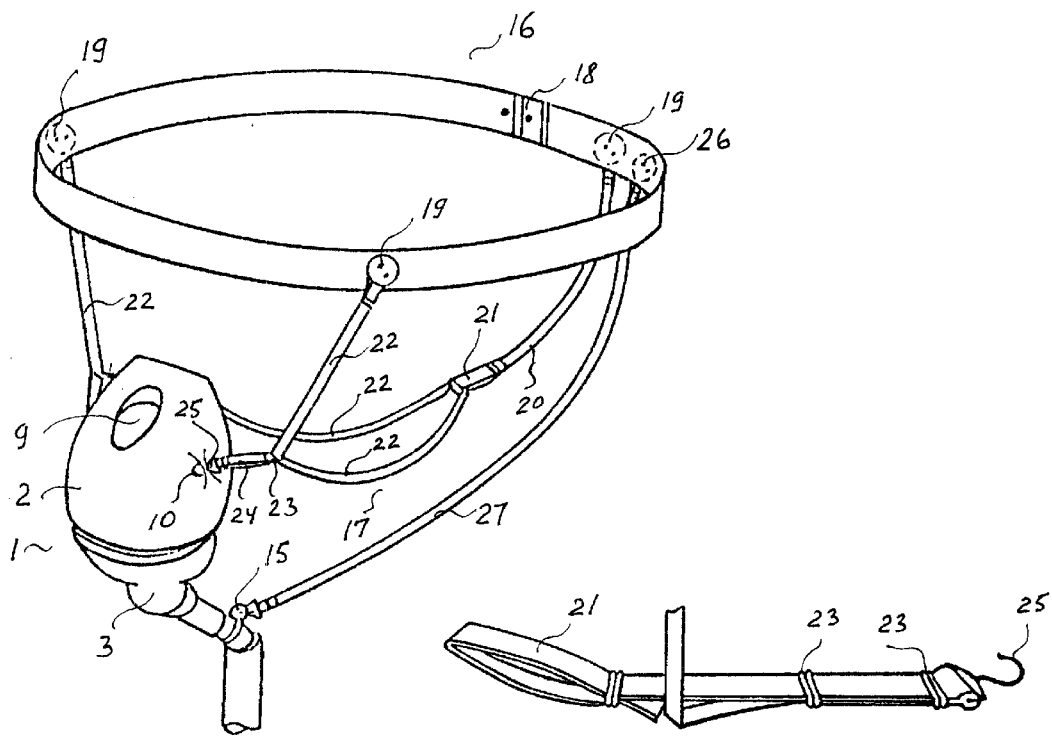
FIG. 2
FIG. 3
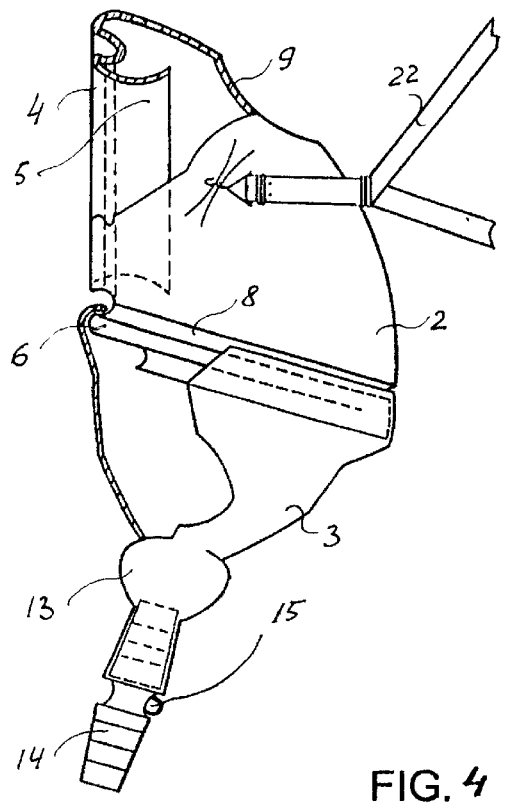
FIG. 4

URINE COLLECTING METHOD AND ASSEMBLY FOR INCONTINENT MALES

BACKGROUND OF THE INVENTION

The present invention relates to the field of medicine, more particularly, to the field of male incontinence commonly resulting as a complication from prostate cancer surgery.

Permanent male incontinence and other types of inability to control the flow of urine from the bladder are common side effects of the prostate cancer surgery. Various devices have heretofore been devised to collect the urine, one type of these devices being a collector device which is typically secured on the patient's body and constantly worn under his cloths.

The simplest and most widely used method of preventing the embarrassing leaks, is wearing specialized adult diapers. However, such diapers can only contain a relatively small amount of urine and, therefore, need to be changed often. Moreover, diapers are uncomfortable for wear in everyday life, especially when a person with incontinence has to work, travel or otherwise be active.

A variety of external catheter-type collecting devices are also known in the art. These external catheters are used to receive the urine into their receptacles and then direct it into a provided collection container. One such known catheter, currently manufactured by Mentor Co., takes the form of an elastic condom-like receptacle provided in its lower portion with a connector tube. The connector tube connects the receptacle with a urine collector, where the collected urine is stored until the collector is emptied and washed. This exterior catheter is typically attached to a male pubic area by an adhesive tape, either provided separately from the catheter or attached to the upper portion of the receptacle. The major drawback of the described catheter is the pain associated with its removal, when the adhesive tape has to be separated from the body. Additionally, because a patient does not spend all of his day standing up, the urine may flow back into the receptacle, for example when the patient sits or lays down, resulting in accumulated moisture surrounding the male organ.

Another catheter-type device is disclosed in U.S. Pat. No. 5,478,334 (the '334 patent), granted to Bernstein on Dec. 26, 1995. The '334 patent teaches a male incontinence catheter having a urostomy pouch urine collector, strapped onto the hips or waist of an incontinent male, combined with an open-ended short condom-like receptacle, the open front end of which is engaging the shaft of the male organ from whose head urine is discharged into the pouch through its inlet. The drawback of the catheter described in the '334 patent is that the male organ is constantly enclosed within the tight and airless condom. This enclosure leads to constant sweating, itching and skin irritation. Moreover, when the patient wearing this catheter changes his body position, for example walks, sits or lays down, the urine from the collector may flow back to the male organ leading to a discomfort or a possible illness, especially in cold climates.

Another known male incontinence device is disclosed in U.S. Pat. No. 5,593,389 (the '389 patent), granted to Chang on Jan. 14, 1997. The '389 patent teaches a more complicated urine collection assembly having a scrotal support and an elastic catheter. The catheter has foam pads impregnated with an antiseptic. One of the drawbacks of this incontinence device is that the male organ is surrounded with wet foam pads of the catheter. Additionally, when the patient sits or lays downs, the urine may flow into the scrotal support. Therefore, the entire skin area of the male organ will be exposed to moisture for extensive periods of time. This is especially uncomfortable during cold seasons and may even lead to various diseases.

Another known male incontinence device is disclosed in U.S. Pat. No. 6,010,489 (the '489 patent), granted to Blackburn on Jan. 4, 2000. The '489 patent teaches an incontinence device having a waistband with a pendant bib attached to it. The bib has a hole with a grommet push-fit into the hole such that the grommet forms an outside flange. A cone-shaped urine collector is attached to the outside flange of the hole to collect the urine of the patient and is secured to the waistband by two belts. The disadvantage of this catheter is that the patient's male organ is constantly surrounded by moisture, especially when the patient is sitting or lying down. Moreover, as the patient's body position changes, the urine may flow between the grommet and the patient's skin causing itching and irritation. Another drawback of the disclosed device is that the simplified support system using two belts attached to the waistband does not provide adequate support for the entire urine collector assembly.

SUMMARY OF THE INVENTION

It is an object of the present invention to provide a male incontinence method and device which will eliminate the above described drawbacks and disadvantages of currently known incontinence devices.

It is another object of the present invention to provide a male incontinence device where the entire surface of a patient's male organ will be kept dry regardless of the patient's body position and orientation.

It is still another object of the present invention to provide a male incontinence device which is hygienic to use.

It is a further object of the present invention to provide a male incontinence device with a reliable, comfortable and adjustable support structure.

Other objects, advantages and features of this invention will be more apparent hereinafter.

The above enumerated objects are accomplished by the provided urine collecting assembly having a urine receptacle and a urine collector. In the preferred embodiment, the urine receptacle comprises a case enclosing the male organ that has an outer vertical flange, an inner vertical flange and an outer horizontal flange. The urine receptacle also has a catheter connected to the case of the receptacle with its inner horizontal flange, this inner horizontal flange being mounted on the outer horizontal flange means of the case. The urine collector of the present invention has a collecting compartment which is connected to the catheter of the receptacle with a connecting tube. In the preferred embodiment, the outer vertical flange of the case of the receptacle is supporting the male organ of the patient and the inner vertical flange of the case and the inner horizontal flange of the catheter are preventing the flow-back of the urine, thereby keeping the pubic area of the patient free of moisture. The provided assembly is preferably secured on the patient's body using a waistband and a belt set, displaced between the waistband and the assembly.

BRIEF DESCRIPTION OF THE DRAWINGS

A full understanding of the invention can be gained from the following description of the preferred embodiment when read in conjunction with the accompanying drawing in which:

FIG. 2 is a front perspective view of the urine collecting assembly (without the urine collector) shown with a waistband and a set of belts;

FIG. 3 is a side perspective view of the adjustable elastic belt attached to the waistband for securing the provided device to the patient's body;

FIG. 4 is a cross-sectional view of the urine collecting assembly in accordance with the present invention;

DETAILED DESCRIPTION OF THE PREFERRED EMBODIMENT AND THE DRAWINGS

Figure 1:
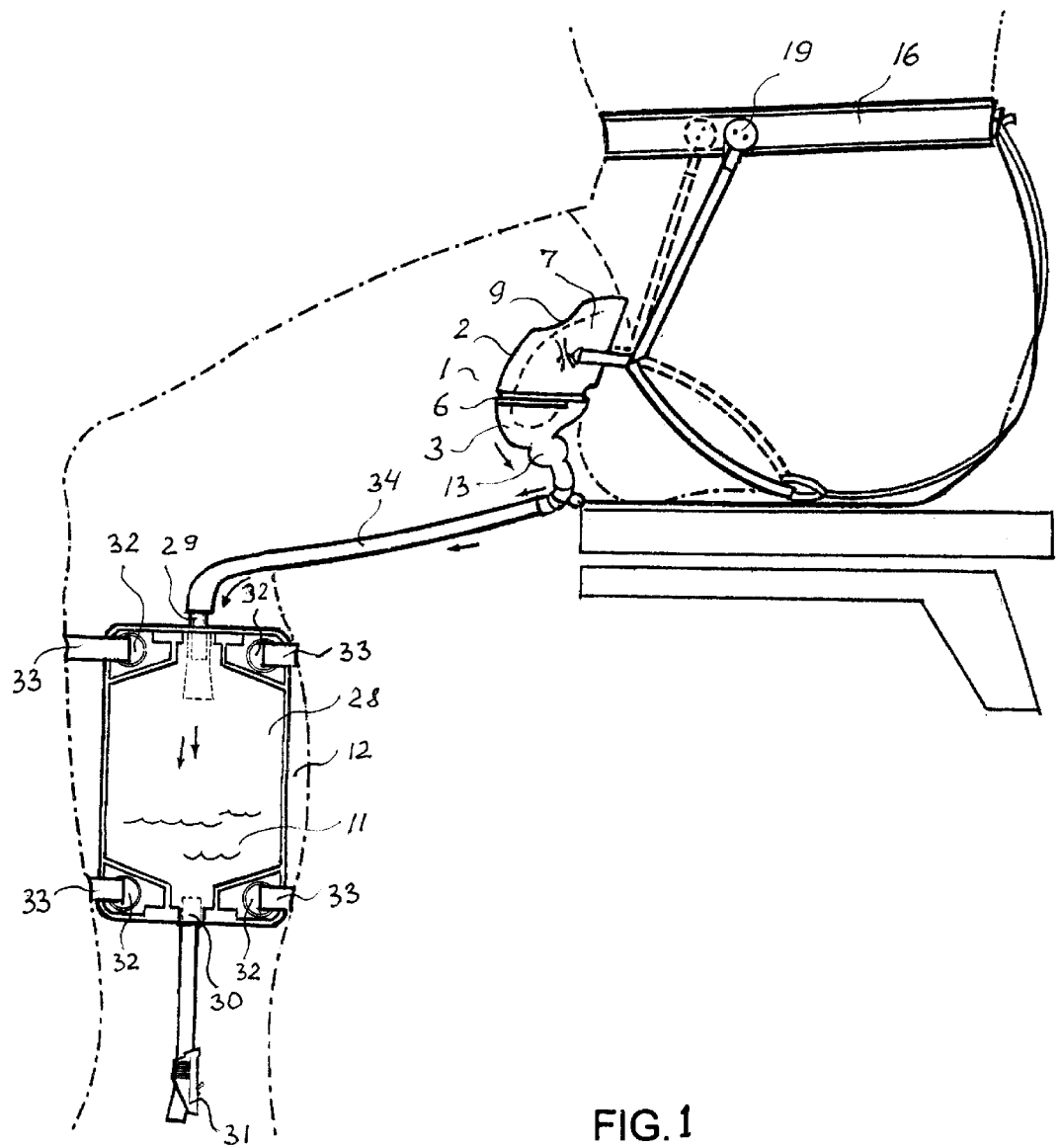
FIG. 1 is a side view of the urine collecting assembly shown secured on the patient's body.
Figure 5:
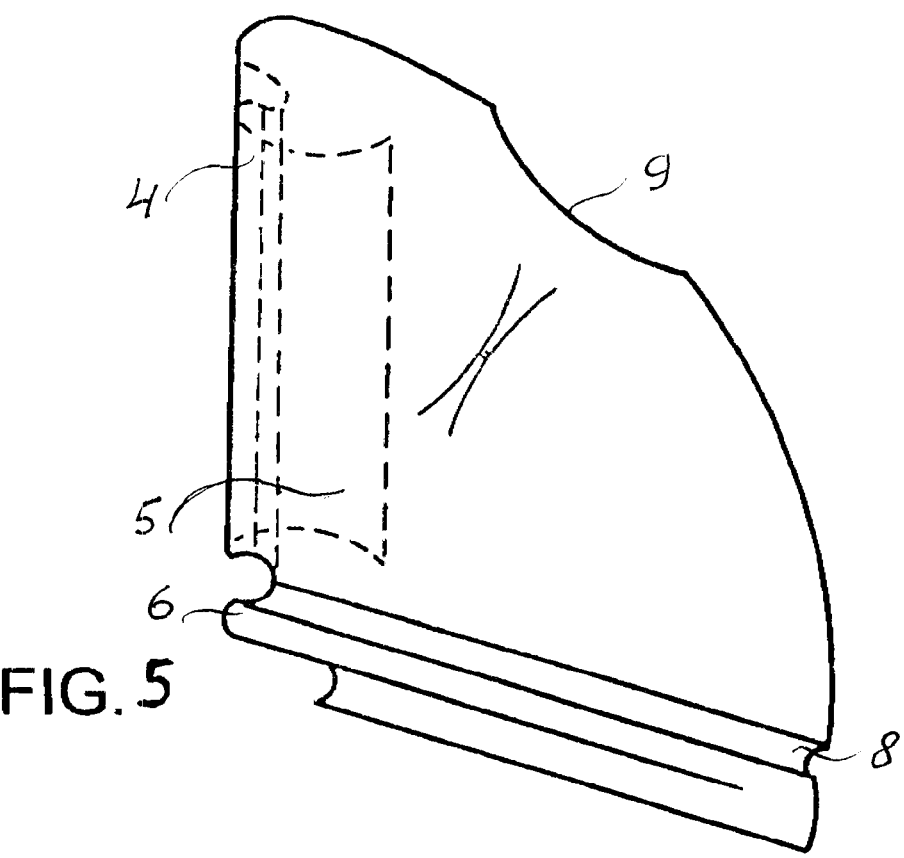
FIG. 5 is a side view of the case of the receptacle of the urine collecting assembly.
Figure 6:
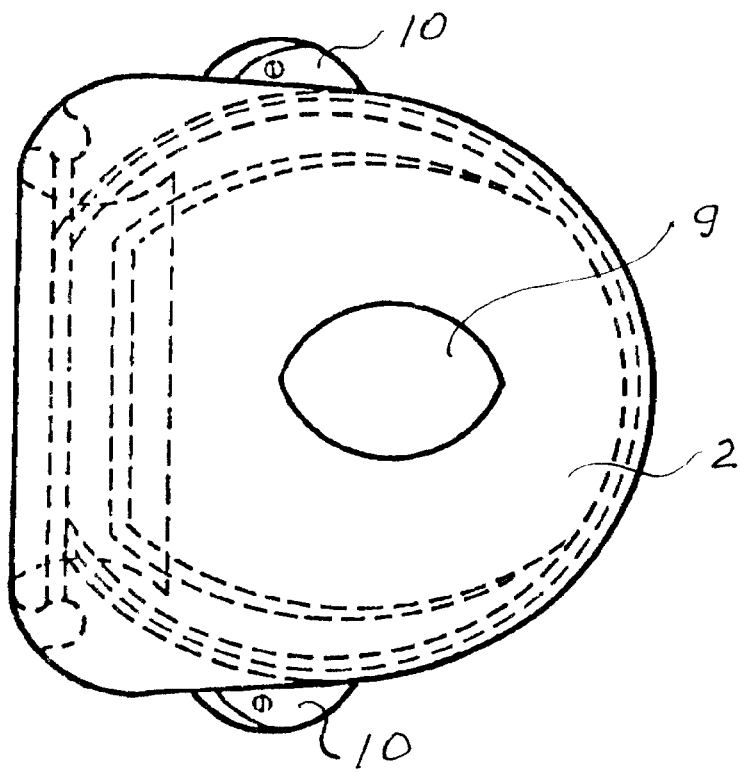
FIG. 6 is a top view of the case of the receptacle of the urine collecting assembly.

In accordance with the preferred embodiment of the present invention shown in FIG. 1, the provided urine collection assembly comprises a urine receptacle 1, a urine collector 12 and a waistband 16 having a belt set 17 for securing the assembly to the patient's body. The urine receptacle 1 preferably has a case 2 and a catheter 3 connected to the case 2. In the preferred embodiment, the case 2 has three flanges. More specifically, the case 2 has an outer vertical flange 4, an inner vertical flange 5 with concave edges, and an outer horizontal flange 6. When the assembly is worn by the patient, the outer vertical flange 4 is located adjacent to the pubic area of the patient's body and serves to position the patient's male organ 7. The inner vertical flange 5 and outer horizontal flange 6 protect the pubic area of the body from the flow-back of the urine regardless of the position of the patient's body (sitting, lying on his back, etc.) The outer horizontal flange 6 is also provided to secure the catheter 3 to the case 2.

The case 2 preferably has an inner horizontal flange 8, located inside and along the ¾ of the length of the outer horizontal flange 6. The flange 8 serves as a support saddle for the catheter 3. Similarly to the inner vertical flange 5, the inner horizontal flange 8 preferably has concave edges and, therefore, it also protects the patient's male organ from the flow-back of the urine in different positions of the patient's body.

The case 2 is preferably provided with an opening 9 in its upper portion. This opening may be used by the patient for personal hygiene, for example to wash the male organ and the inside of the assembly using a rubber pear. The opening also provides airflow to the male organ ventilating the inside of the assembly and eliminating moisture vapors. The opening 9 may be closed with a provided cap (not shown) if necessary. Additionally, the case 2 is preferably provided with two hinges 10, preferably located on the sides of the case. In the preferred embodiment, the case 2 is made entirely of plastic material.

The provided catheter 3 has a curved surface preferably sloped toward the patient's body. The catheter 3 receives the urine 11 from male organ 7 and conveys it to the urine collector 12. The lower portion of the catheter 3 is preferably constructed as a spherical compartment 13 with a tip 14. The spherical compartment 13 prevents the fast flowing urine from accumulating in the narrow tip 14. There is preferably a hinge 15 on the outside of the tip 14. Catheter 3 is preferably made of an elastic material, for example rubber, silicone or polyurethane. An optional variation in the design of the catheter 3 (not shown on the drawings) includes an adjustable length of its main body so it can be attached to the horizontal flange 6 leaving just enough length to fit the male organ 7. This design is similar to the unfoldable concept of the male condom so it can accommodate male organs of various sizes.

The belt set 17 preferably comprises a back belt 20, two supporting belts 22 and an adjustment belt 27. The waistband 16 with the belt set 17 is used in the preferred embodiment to secure the receptacle 1 in the pubic area of the patient. The waistband is preferably worn around the patient's waist over underwear with a central opening (underwear is not shown). The waistband 16 is preferably equipped with a lock 18, which can adjust the length of the waistband. Several buttons 19 are located on the waistband 16. Two of the provided buttons 19 are preferably located along the front portion of the waistband 16, and at least one button 19 is located on the back of the waistband. The back belt 20 is fastened with one end to the button 19 located on the back of the waistband. The other end of the back belt 20 is provided with a loop 21. Supporting belts 22 are fastened with their top ends to the two buttons 19 located along the front portion of the waistband 16. The bottom ends of both supporting belts 22 are fastened to the loop 21. Additionally, fasteners 23 are used to form loops 24 in the middle portion of each supporting belt 22. Each loop 24 is provided with a hook 25 for securing of each supporting belt 22 to one of hinges 10 of the case 2.

Another button 26 is provided on the back of the waistband 16. The button 26 allows one end of the adjustment belt 27 to be secured to the waistband 16. The other end of the adjustment belt 27 is connected to the hinge 15 of the tip 14. Belt 27 allows the patient to adjust the position of the male organ by pulling on the belt 27.

All belts of the belt set 17 are preferably made of an elastic material, for example rubber.

The urine collector 12 preferably comprises a compartment 28 with a tip 29 in its upper portion and a tip 30 with a drain clamp 31 in its lower portion. As is obvious to one of ordinary skill in the art, any other known drainage devices may be utilized in place of the drain clamp 31 to empty the urine collector 12. Four openings 32 are provided at four corners of the compartment 28. Belts 33 are inserted into the openings 32 and fastened around the patient's leg.

The receptacle 1 is connected to the collector 12 through a tube 34. The top end of the tube 34 is secured to the tip 14 of the catheter 3. The bottom end of the tube 34 is mounted on the tip 29 of the urine collector 12. The urine collector 12 is preferably made of a waterproof material, for example rubber.

In use and according to the method of the invention, the urine receptacle 1 is secured in the pubic area of the patient's body using the waistband 16 with the belt set 17. Waistband 16 is worn over the provided underwear with a central opening. Patient's male organ 7 protrudes through the central opening of the underwear, outer vertical flange 4 and inner vertical flange 5 of the case 2 and freely hangs in the inner space of the catheter 3. At the same time, the urine collector 12 is secured on the patient's leg using belts 33.

As the urine 11 flows from the patient's male organ 7, it is conveyed from the spherical compartment 13 of the catheter 3, through the tip 14, connecting tube 34 and tip 29 into the compartment 28 of the urine collector 12. As the urine collector fills with urine, the compartment 28 can be drained by opening the drain clamp 31.

The above described urine collecting assembly may be used by a male patient regardless of his position. When the patient is lying on his back, the flow-back and spilling of the urine is prevented by the inner vertical flange 5, outer horizontal flange 6, and closing of the opening 9 with a cap. Any urine coming back towards the pubic area is trapped in the cavities formed by concave edges of the inner vertical and horizontal flanges 5 and 6. Upon subsequent return to a vertical position, the urine will be drained down from these cavities towards the urine collector 12. Concave edges of the flange 5 do not allow the urine to reach the pubic area of the patient. When the patient is lying in his side, then, in addition to the flange 6, the flow-back of the urine is prevented by similarly constructed inner vertical flange 5. As described above, the flange 5 has concave edges along the entire length of its edges, in contrast to the flange 6, which has a concave edge only along ¾ of the length of its edge. Therefore, flanges 5 and 6 provide double protection of the pubic area of the patient from the urine moisture regardless of the patient's position.

Having described this invention with regard to specific embodiments, it is to be understood that the description is not meant as a limitation since further variations or modifications may be apparent or may suggest themselves to those skilled in the art. Although the urine collecting assembly is described with a belt support other known support mechanisms may be utilized with the provided assembly. It is intended that the present application cover such variations and modifications as fall within the scope of the appended claims.

I claim as follows:

1. A urine collecting assembly comprising:
   a urine receptacle, said urine receptacle further comprising a case configured to accept a male organ of a patient and having an outer vertical flange means, an inner vertical flange means and an outer horizontal flange means, and a catheter having an inner horizontal flange means, said inner horizontal flange means of said catheter being mounted on said outer horizontal flange means of said case;
   a urine collector, said urine collector further comprising a collecting compartment;
   a connecting means, said connecting means connecting said catheter of said receptacle to said collecting compartment of said urine collector, wherein said outer vertical flange means of said case is configured to support said male organ and wherein said inner vertical flange means and said inner horizontal flange means are configured to prevent flow-back of the urine.

2. The urine collecting assembly according to claim 1, wherein said inner vertical flange means of said case comprises a concave edge, said concave edge being located along an entire length of said inner vertical flange means.

3. The urine collecting assembly according to claim 1, wherein said inner horizontal flange means of said catheter comprises a concave edge, said concave edge being located along ¾ of a length of said inner horizontal flange means.

4. The urine collecting assembly according to claim 1 wherein said catheter further comprises a spherical compartment, said spherical compartment being configured to prevent accumulation of urine in said catheter.

5. The urine collecting assembly according to claim 1, wherein said connection means further comprise a connection tube, said connection tube displaced between said catheter of said urine receptacle and said collecting compartment of said urine collector.

6. The urine collecting assembly according to claim 1 wherein said catheter of said urine receptacle is made of an elastic material.

7. A method of collecting urine into a urine collection assembly comprising the steps of:
   a. providing a urine assembly collector to the incontinence patient, said urine assembly collector comprising a urine receptacle and a urine collector, said urine receptacle further comprising a case enclosing the male organ of the patient and having an outer vertical flange, an inner vertical flange and an outer horizontal flange, and a catheter having an inner horizontal flange, said inner horizontal flange of said catheter being mounted on said outer horizontal flange of said case;
   b. securing said urine collection assembly on the patient's body by using a waistband and a plurality of belts connected to said waistband and said urine collection assembly;
   c. receiving the patient's urine into said urine receptacle;
   d. directing said urine from said urine receptacle through said catheter and into said urine collector, said catheter being connected to said urine collector; and
   e. preventing flow-back of the patient's urine from said urine collector into said urine receptacle by using said inner vertical flange of said case and said inner horizontal flange of said catheter.

8. The method of collecting urine into a urine collection assembly according to claim 7 further comprising the step of emptying said urine collector.

\* \* \* \* \*